US012268525B2

(12) United States Patent
Linder et al.

(10) Patent No.: US 12,268,525 B2
(45) Date of Patent: Apr. 8, 2025

(54) CATHETER FOR IMAGING AND MEASUREMENT OF PRESSURE AND OTHER PHYSIOLOGICAL PARAMETERS

(71) Applicant: XENTER, INC., Salt Lake City, UT (US)

(72) Inventors: Richard J. Linder, Sandy, UT (US); Cory Rex Estes, Mapleton, UT (US); Scott Kenneth Marland, Bountiful, UT (US); Edwin Meade Maynard, Salt Lake City, UT (US); Steven Matthew Quist, Salt Lake City, UT (US); Nathan J. Knighton, Syracuse, UT (US)

(73) Assignee: XENTER, INC., Salt Lake City, UT (US)

( * ) Notice: Subject to any disclaimer, the term of this patent is extended or adjusted under 35 U.S.C. 154(b) by 0 days.

(21) Appl. No.: 18/074,126

(22) Filed: Dec. 2, 2022

(65) Prior Publication Data

US 2023/0109126 A1     Apr. 6, 2023

Related U.S. Application Data

(63) Continuation of application No. 17/205,854, filed on Mar. 18, 2021, now Pat. No. 11,540,776.
(Continued)

(51) Int. Cl.
*A61B 5/00*      (2006.01)
*A61B 5/0215*    (2006.01)
(Continued)

(52) U.S. Cl.
CPC .......... *A61B 5/6852* (2013.01); *A61B 5/0002* (2013.01); *A61B 5/0215* (2013.01);
(Continued)

(58) Field of Classification Search
CPC ..... A61B 5/6852; A61B 5/0215; A61M 25/09
See application file for complete search history.

(56) References Cited

U.S. PATENT DOCUMENTS

| 4,595,012 A | 6/1986 | Webler et al. |
|---|---|---|
| 4,827,941 A | 5/1989 | Taylor et al. |

(Continued)

FOREIGN PATENT DOCUMENTS

| CN | 103720463 A | 4/2014 |
|---|---|---|
| CN | 105212902 A | 1/2016 |

(Continued)

OTHER PUBLICATIONS

Aldaoud, et al. "A stent-based power and data link for sensing intravascular biological indicators." IEEE Sensors Letters 2.4 (2018): 1-4.
(Continued)

*Primary Examiner* — Daniel L Cerioni
(74) *Attorney, Agent, or Firm* — Workman Nydegger

(57) ABSTRACT

A catheter system includes an elongated tube structure configured for insertion into a luminal space, such as the vasculature, of a body. The catheter is conductive and configured to conduct electrical signals. The catheter includes one or more power and data coupling devices configured to send and receive power and/or data signals, such as from an underlying guidewire disposed within a lumen of the catheter. One or more sensors are coupled to a distal section of the catheter and are electrically connected to the one or more power and data coupling devices.

14 Claims, 11 Drawing Sheets

Related U.S. Application Data

(60) Provisional application No. 63/044,960, filed on Jun. 26, 2020, provisional application No. 62/992,695, filed on Mar. 20, 2020.

(51) Int. Cl.

| | | |
|---|---|---|
| *A61B 5/07* | (2006.01) | |
| *A61M 25/09* | (2006.01) | |
| *H02J 50/05* | (2016.01) | |
| *H02J 50/40* | (2016.01) | |
| *H02J 50/90* | (2016.01) | |
| *A61B 1/05* | (2006.01) | |
| *A61B 8/12* | (2006.01) | |
| *A61M 25/01* | (2006.01) | |

(52) U.S. Cl.
CPC ............ *A61B 5/02158* (2013.01); *A61B 5/07* (2013.01); *A61B 5/6851* (2013.01); *A61M 25/09* (2013.01); *H02J 50/05* (2016.02); *H02J 50/402* (2020.01); *H02J 50/90* (2016.02); *A61B 1/05* (2013.01); *A61B 5/0059* (2013.01); *A61B 8/12* (2013.01); *A61B 2503/40* (2013.01); *A61B 2560/0214* (2013.01); *A61B 2560/0219* (2013.01); *A61B 2562/0247* (2013.01); *A61B 2562/06* (2013.01); *A61B 2562/222* (2013.01); *A61M 2025/0183* (2013.01)

(56) References Cited

U.S. PATENT DOCUMENTS

| | | | |
|---|---|---|---|
| 4,850,358 A | 7/1989 | Millar | |
| 4,917,104 A | 4/1990 | Rebell | |
| 5,154,725 A | 10/1992 | Leopold | |
| 5,366,490 A | 11/1994 | Edwards et al. | |
| 5,368,035 A | 11/1994 | Hamm et al. | |
| 5,564,434 A | 10/1996 | Halperin et al. | |
| 5,651,767 A | 7/1997 | Schulman et al. | |
| 5,790,081 A | 8/1998 | Unwin | |
| 5,814,089 A | 9/1998 | Stokes et al. | |
| 5,860,974 A | 1/1999 | Abele | |
| 6,004,269 A | 12/1999 | Crowley et al. | |
| 6,167,763 B1 | 1/2001 | Tenerz et al. | |
| 6,211,799 B1 | 4/2001 | Post et al. | |
| 6,245,020 B1 | 6/2001 | Moore et al. | |
| 6,248,076 B1 | 6/2001 | White et al. | |
| 6,479,785 B1 | 11/2002 | Fugo et al. | |
| 6,728,571 B1 | 4/2004 | Barbato | |
| 7,210,940 B2 | 5/2007 | Baily et al. | |
| 7,645,233 B2 | 1/2010 | Tulkki et al. | |
| 7,651,578 B2 | 1/2010 | Sharrow et al. | |
| 8,076,821 B2 | 12/2011 | Degertekin | |
| 8,277,386 B2 | 10/2012 | Ahmed et al. | |
| 8,362,673 B2 | 1/2013 | Hsu | |
| 8,473,067 B2 | 6/2013 | Hastings et al. | |
| 8,478,384 B2 | 7/2013 | Schmitt et al. | |
| 8,617,088 B2 | 12/2013 | Samuelsson et al. | |
| 8,882,763 B2 | 11/2014 | Stevenson et al. | |
| 9,106,270 B2 | 8/2015 | Puterbaugh et al. | |
| 9,192,306 B2 | 11/2015 | Chen | |
| 9,259,206 B2 | 2/2016 | Degertekin et al. | |
| 9,486,355 B2 | 11/2016 | Gustus et al. | |
| 9,667,323 B2 | 5/2017 | Habraken et al. | |
| 9,675,325 B2 | 6/2017 | Moore et al. | |
| 10,028,667 B2 | 7/2018 | Kishida et al. | |
| 10,080,872 B2 | 9/2018 | Webler | |
| 10,206,556 B2 | 2/2019 | Matsuki et al. | |
| 10,390,791 B2 | 8/2019 | Courtney et al. | |
| 10,391,292 B2 | 8/2019 | Sutton | |
| 10,418,755 B2 | 9/2019 | Kahlman | |
| 10,463,259 B2 | 11/2019 | Glover et al. | |
| 10,463,274 B2 | 11/2019 | Kassab et al. | |
| 10,531,841 B2 | 1/2020 | Merritt et al. | |
| 10,569,072 B2 | 2/2020 | Agrawal et al. | |
| 10,737,086 B2 | 8/2020 | Agrawal et al. | |
| 10,765,853 B2 | 9/2020 | Neff et al. | |
| 10,842,981 B2 | 11/2020 | Agrawal et al. | |
| 10,869,603 B2 | 12/2020 | Millett et al. | |
| 10,881,846 B2 | 1/2021 | Furnish et al. | |
| 11,259,877 B2 | 3/2022 | Kahya et al. | |
| 11,304,659 B2 | 4/2022 | Linder et al. | |
| 2001/0001317 A1 | 5/2001 | Duerig et al. | |
| 2001/0029337 A1 | 10/2001 | Pantages et al. | |
| 2001/0045899 A1 | 11/2001 | Hoek | |
| 2002/0013527 A1 | 1/2002 | Hoek et al. | |
| 2002/0151823 A1 | 10/2002 | Miyata et al. | |
| 2003/0083723 A1 | 5/2003 | Wilkinson et al. | |
| 2003/0120271 A1 | 6/2003 | Burnside et al. | |
| 2004/0064024 A1 | 4/2004 | Sommer | |
| 2004/0153136 A1 | 8/2004 | Vardi et al. | |
| 2005/0143664 A1 | 6/2005 | Chen et al. | |
| 2006/0009817 A1 | 1/2006 | Tulkki | |
| 2006/0264925 A1 | 11/2006 | Sharareh et al. | |
| 2007/0118035 A1 | 5/2007 | Secora | |
| 2007/0191830 A1 | 8/2007 | Crompton et al. | |
| 2007/0233045 A1 | 10/2007 | Weitzner et al. | |
| 2007/0255166 A1 | 11/2007 | Carney et al. | |
| 2008/0021336 A1 | 1/2008 | Dobak, III | |
| 2008/0177183 A1 | 7/2008 | Courtney et al. | |
| 2008/0249515 A1 | 10/2008 | Taylor | |
| 2009/0005859 A1 | 1/2009 | Keilman | |
| 2009/0062739 A1 | 3/2009 | Anderson | |
| 2009/0110148 A1 | 4/2009 | Zhang et al. | |
| 2009/0131798 A1 | 5/2009 | Minar et al. | |
| 2009/0156926 A1 | 6/2009 | Messerly et al. | |
| 2009/0171345 A1 | 7/2009 | Miller et al. | |
| 2009/0259772 A1 | 10/2009 | Ketko et al. | |
| 2009/0284332 A1 | 11/2009 | Moore et al. | |
| 2010/0070007 A1 | 3/2010 | Parker et al. | |
| 2010/0087143 A1 | 4/2010 | Bonin | |
| 2010/0113939 A1 | 5/2010 | Mashimo et al. | |
| 2010/0174233 A1 | 7/2010 | Kuban et al. | |
| 2010/0305476 A1 | 12/2010 | Thornton et al. | |
| 2011/0190756 A1 | 8/2011 | Venkatachalam et al. | |
| 2011/0213220 A1 | 9/2011 | Samuelsson et al. | |
| 2011/0257511 A1 | 10/2011 | Krueger | |
| 2011/0270369 A1 | 11/2011 | Tekmen et al. | |
| 2012/0130230 A1 | 5/2012 | Eichler et al. | |
| 2012/0209061 A1 | 8/2012 | Kato | |
| 2013/0064043 A1 | 3/2013 | Degertekin et al. | |
| 2013/0109980 A1 | 5/2013 | Teo | |
| 2013/0123638 A1 | 5/2013 | Tom et al. | |
| 2013/0172782 A1 | 7/2013 | Hilmersson | |
| 2013/0190726 A1 | 7/2013 | Kesner et al. | |
| 2013/0204111 A1 | 8/2013 | Flanders | |
| 2013/0289424 A1 | 10/2013 | Brockway et al. | |
| 2013/0296692 A1 | 11/2013 | Vanney et al. | |
| 2014/0066705 A1 | 3/2014 | Robertson et al. | |
| 2014/0142398 A1 | 5/2014 | Patil et al. | |
| 2014/0171788 A1 | 6/2014 | Stigall | |
| 2014/0180031 A1 | 6/2014 | Anderson | |
| 2014/0187978 A1 | 7/2014 | Millett et al. | |
| 2014/0187979 A1 | 7/2014 | Burkett | |
| 2014/0236017 A1 | 8/2014 | Degertekin et al. | |
| 2014/0248801 A1 | 9/2014 | Riezebos et al. | |
| 2014/0323860 A1 | 10/2014 | Courtney et al. | |
| 2015/0074995 A1 | 3/2015 | Patil et al. | |
| 2015/0141854 A1 | 5/2015 | Eberle et al. | |
| 2015/0196210 A1 | 7/2015 | McCaffrey | |
| 2015/0208901 A1 | 7/2015 | Gazdzinski | |
| 2015/0216403 A1 | 8/2015 | Whitmore, III | |
| 2015/0265181 A1 | 9/2015 | Flanders | |
| 2015/0305708 A1 | 10/2015 | Stigall et al. | |
| 2015/0313478 A1 | 11/2015 | Veszelei et al. | |
| 2016/0249817 A1 | 9/2016 | Mazar et al. | |
| 2016/0262698 A1 | 9/2016 | Mahlin | |
| 2016/0310020 A1 | 10/2016 | Warnking et al. | |
| 2017/0136496 A1 | 5/2017 | Jacobs et al. | |
| 2017/0164867 A1 | 6/2017 | Kassab et al. | |
| 2017/0164925 A1 | 6/2017 | Marshall et al. | |
| 2017/0189669 A1 | 7/2017 | Kamarajugadda et al. | |
| 2017/0215801 A1 | 8/2017 | Jung et al. | |

(56) References Cited

U.S. PATENT DOCUMENTS

| | | |
|---|---|---|
| 2017/0266433 A1 | 9/2017 | Daniels et al. |
| 2018/0099125 A1 | 4/2018 | Richer et al. |
| 2018/0125365 A1 | 5/2018 | Hunter et al. |
| 2018/0262236 A1 | 9/2018 | Kahlman |
| 2018/0263515 A1 | 9/2018 | Raval |
| 2019/0053787 A1 | 2/2019 | Stigall et al. |
| 2019/0070402 A1 | 3/2019 | Isaacson |
| 2019/0133462 A1 | 5/2019 | Millett et al. |
| 2019/0167351 A1 | 6/2019 | Salazar et al. |
| 2019/0184159 A1 | 6/2019 | Yeh et al. |
| 2019/0247618 A1 | 8/2019 | Shellhammer et al. |
| 2019/0290139 A1 | 9/2019 | Sio et al. |
| 2019/0290368 A1 | 9/2019 | West et al. |
| 2019/0298182 A1 | 10/2019 | Syed et al. |
| 2019/0358387 A1 | 11/2019 | Elbadry et al. |
| 2019/0380651 A1 | 12/2019 | Carreel et al. |
| 2020/0022587 A1 | 1/2020 | Glover et al. |
| 2020/0054227 A1 | 2/2020 | Van Rens |
| 2020/0060577 A1 | 2/2020 | Kassab et al. |
| 2021/0030364 A1 | 2/2021 | Burkett et al. |
| 2021/0290059 A1 | 9/2021 | Linder et al. |
| 2021/0290100 A1 | 9/2021 | Linder et al. |
| 2021/0290164 A1 | 9/2021 | Linder et al. |
| 2021/0290198 A1 | 9/2021 | Linder et al. |
| 2022/0047845 A1 | 2/2022 | Niederhauser et al. |
| 2022/0133236 A1 | 5/2022 | Linder et al. |
| 2022/0160306 A1 | 5/2022 | Linder et al. |
| 2022/0202368 A1 | 6/2022 | Linder et al. |
| 2022/0361743 A1 | 11/2022 | Chan et al. |
| 2024/0115205 A1 | 4/2024 | Linder et al. |

FOREIGN PATENT DOCUMENTS

| | | |
|---|---|---|
| CN | 105919559 | 9/2016 |
| DE | 19621003 | 1/1997 |
| JP | 09-512470 A | 12/1997 |
| JP | 2014-530639 A | 11/2014 |
| JP | 2015-501193 A | 1/2015 |
| JP | 2015-061314 A | 3/2015 |
| JP | 2016-509497 A | 3/2016 |
| JP | 2017-501755 A | 1/2017 |
| JP | 2016-518870 A | 3/2017 |
| JP | 2017-508574 A | 3/2017 |
| JP | 2018-524076 A | 8/2018 |
| JP | 2018-140180 A | 9/2018 |
| WO | 2012/173697 A1 | 12/2012 |
| WO | 2016/130713 A1 | 8/2016 |
| WO | 2016/209665 A1 | 12/2016 |
| WO | 2018/017547 | 1/2018 |
| WO | 2020/030776 A1 | 2/2020 |

OTHER PUBLICATIONS

Degertekin FL, Guldiken RO, Karaman M. Annular-ring CMUT arrays for forward-looking IVUS: transducer characterization and imaging. IEEE Trans Ultrason Ferroelectr Freq Control. Feb. 2006;53(2):474-82.

E. F. Arkan and F. L. Degertekin, "Analysis and Design of High-Frequency 1-D CMUT Imaging Arrays in Noncollapsed Mode," in IEEE Transactions on Ultrasonics, Ferroelectrics, and Frequency Control, vol. 66, No. 2, pp. 382-393, Feb. 2019.

Final Office Action received for U.S. Appl. No. 17/205,754, mailed on Aug. 25, 2021, 12 pages.

Final Office Action received for U.S. Appl. No. 17/205,854, mailed on Sep. 23, 2021, 14 pages.

G. Jung, C. Tekes, A. Pirouz, F. L. Degertekin and M. Ghovanloo, "Supply-Doubled Pulse-Shaping High Voltage Pulser for CMUT Arrays," in IEEE Transactions on Circuits and Systems II: Express Briefs, vol. 65, No. 3, pp. 306-310, Mar. 2018.

Gurun G, Hasler P, Degertekin F. Front-end receiver electronics for high-frequency monolithic CMUT-on-CMOS imaging arrays. IEEE Transactions on Ultrasonics, Ferroelectrics, and Frequency Control. Aug. 2011;58(8):1658-1668.

Gurun G, Tekes C, Zahorian J, Xu T, Satir S, Karaman M, Hasler J, Degertekin FL. Single-chip CMUT-on-CMOS front-end system for real-time volumetric IVUS and ICE imaging. IEEE Trans Ultrason Ferroelectr Freq Control. Feb. 2014;61(2):239-50.

International Search Report and Written Opinion received for PCT Patent Application No. PCT/US21/023198, mailed on Jun. 14, 2021, 2 pages.

International Search Report and Written Opinion received for PCT Patent Application No. PCT/US21/23135, mailed on Jun. 8, 2021, 8 pages.

International Search Report and Written Opinion received for PCT Patent Application No. PCT/US21/23148, mailed on Jun. 4, 2021, 7 pages.

International Search Report and Written Opinion received for PCT Patent Application No. PCT/US21/23184, mailed on Jun. 7, 2021, 10 pages.

J. Lim, C. Tekes, E. F. Arkan, A. Rezvanitabar, F. L. Degertekin and M. Ghovanloo, "Highly Integrated Guidewire Ultrasound Imaging System-on-a-Chip," in IEEE Journal of Solid-State Circuits, vol. 55, No. 5, pp. 1310-1323, May 2020.

J. Lim, C. Tekes, F. L. Degertekin and M. Ghovanloo, "Towards a Reduced-Wire Interface for CMUT-Based Intravascular Ultrasound Imaging Systems," in IEEE Transactions on Biomedical Circuits and Systems, vol. 11, No. 2, pp. 400-410, Apr. 2017.

J. Zahorian et al., "Monolithic CMUT-on-CMOS Integration for Intravascular Ultrasound Applications," in IEEE Transactions on Ultrasonics, Ferroelectrics, and Frequency Control, vol. 58, No. 12, pp. 2659-2667, Dec. 2011.

Lim J, Arkan EF, Degertekin FL, Ghovanloo M. Toward a reduced-wire readout system for ultrasound imaging. Annu Int Conf IEEE Eng Med Biol Soc. 2014;2014:5080-4.

Lim J, Rezvanitabar A, Degertekin FL, Ghovanloo M. An Impulse Radio PWM-Based Wireless Data Acquisition Sensor Interface. IEEE Sens J. Jan. 15, 2019;19(2):603-614.

Lu, et al. "A review on the recent development of capacitive wireless power transfer technology." Energies 10.11 (2017): 1752.

Non-Final Office Action received for U.S. Appl. No. 17/205,854, mailed on May 19, 2022, 17 pages.

Non-Final Office Action received for U.S. Appl. No. 17/578,373, mailed on Dec. 30, 2022, 11 pages.

Non-Final Office Action received for U.S. Appl. No. 17/205,964, mailed on May 24, 2021.

Pirouz, A.; Degertekin, F.L. An Analysis Method for Capacitive Micromachined Ultrasound Transducer (CMUT) Energy Conversion during Large Signal Operation. Sensors 2019, 19, 876.

S. Satir and F. L. Degertekin, "A nonlinear lumped model for ultrasound systems using CMUT arrays," in IEEE Transactions on Ultrasonics, Ferroelectrics, and Frequency Control, vol. 62, No. 10, pp. 1865-1879, Oct. 2015.

S. Satir, J. Zahorian and F. L. Degertekin, "A large-signal model for CMUT arrays with arbitrary membrane geometry operating in non-collapsed mode," in IEEE Transactions on Ultrasonics, Ferroelectrics, and Frequency Control, vol. 60, No. 11, pp. 2426-2439, Nov. 2013.

Satir S, Degertekin FL. Phase and Amplitude Modulation Methods for Nonlinear Ultrasound Imaging With CMUTs. IEEE Trans Ultrason Ferroelectr Freq Control. Aug. 2016;63(8):1086-92.

Sharei, et al. "Data communication pathway for sensing guidewire at proximal side: A review." Journal of Medical Devices 11.2 (2017).

Tanase et al. "Multi-parameter sensor system with intravascular navigation for catheter/guide wire application", Sensors and Actuators A: Physical vols. 97-98, Apr. 1, 2002, pp. 116-124.

Tekes C, Zahorian J, Gurun G, et al. Volumetric imaging using single chip integrated CMUT-on-CMOS IVUS array. Annu Int Conf IEEE Eng Med Biol Soc. 2012;2012:3195-3198.

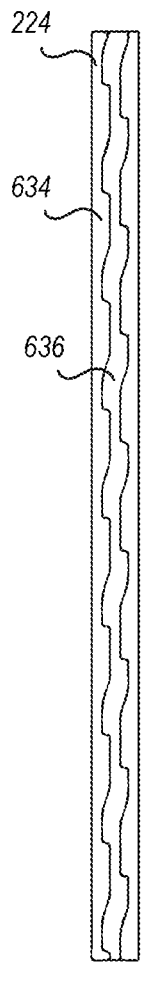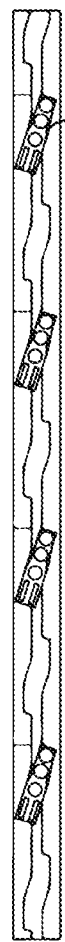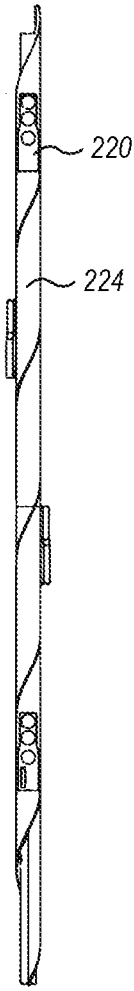
*FIG. 6A*  *FIG. 6B*  *FIG. 6C*  *FIG. 6D*

CATHETER FOR IMAGING AND MEASUREMENT OF PRESSURE AND OTHER PHYSIOLOGICAL PARAMETERS

CROSS-REFERENCE TO RELATED APPLICATIONS

This application is a continuation of U.S. application Ser. No. 17/205,854, filed Mar. 18, 2021 and titled "CATHETER FOR IMAGING AND MEASUREMENT OF PRESSURE AND OTHER PHYSIOLOGICAL PARAMETERS," which claims priority to U.S. Provisional Patent Application No. 62/992,695, filed Mar. 20, 2020 and titled "CATHETER SYSTEM, DEVICE, AND METHOD THEREOF," and to U.S. Provisional Patent Application No. 63/044,960, filed Jun. 26, 2020 and titled "CATHETER AND GUIDEWIRE SYSTEMS WITH ENHANCED LOCATION AND CHARACTERIZATION FEATURES." Each of the foregoing applications is incorporated herein by reference in its entirety.

Additionally, the present application is related to: U.S. patent application Ser. No. 17/205,614 filed Mar. 18, 2021, entitled "SIGNAL CONDUCTING DEVICE FOR CONCURRENT POWER AND DATA TRANSFER TO AND FROM UN-WIRED SENSORS ATTACHED TO A MEDICAL DEVICE", patented as U.S. Pat. No. 11,241,196; U.S. patent application Ser. No. 17/205,754 filed Mar. 18, 2021, entitled "OPERATIVELY COUPLED DATA AND POWER TRANSFER DEVICE FOR MEDICAL GUIDEWIRES AND CATHETERS WITH SENSORS", patented as U.S. Pat. No. 11,304,659; and U.S. patent application Ser. No. 17/205,964 filed Mar. 18, 2021, entitled "GUIDEWIRE FOR IMAGING AND MEASUREMENT OF PRESSURE AND OTHER PHYSIOLOGICAL PARAMETERS", patented as U.S. Pat. No. 11,259,750. Each of the foregoing applications is incorporated herein by reference in its entirety.

BACKGROUND

The present invention relates generally to medical devices, including intraluminal devices such as guidewires and catheters that include various sensors for simultaneous and/or continuous measuring of one or more physiological parameters.

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. Guidewires are available with various outer diameter sizes. Widely utilized sizes include 0.010, 0.014, 0.016, 0.018, 0.024, and 0.035 inches in diameter, for example, though they may also be smaller or larger in diameter. Catheters also come in a variety of sizes and are typically configured to be used with standard guidewire sizes.

In many instances, a guidewire is placed within the body during the interventional procedure where it can be used to guide multiple catheters or other interventional devices to the targeted anatomical location. Once in place, a catheter can be used to aspirate clots or other occlusions, or to deliver drugs, stents, embolic devices, radiopaque dyes, or other devices or substances for treating the patient.

These types of interventional devices can include sensors located at the distal end in order to provide added functionality to the device. For example, intravascular ultrasound (IVUS) is an imaging technique that utilizes a catheter with an ultrasound imaging sensor attached to the distal end. Ultrasound is utilized to image within targeted vasculature (typically the coronary arteries).

The use of such sensors introduces several challenges. In particular, the interventional devices involved have very limited space to work in, given the stringent dimensional constraints involved. Moreover, integrating the sensors with the interventional device in a way that maintains effective functionality can be challenging.

Another issue common to the field is proper localization and positioning of the distal end of the device at the target location. If the device tip is improperly positioned during insertion, or if the tip migrates away from the desired position after insertion, various risks can arise. For catheter implementations, for example, improper positioning can lead to fluid infusions that can cause pain or injury to the patient, increased thrombosis rates, delays in therapy, device breakage or malfunction, delays due to device replacement, and additional costs associated with the device replacement and the additional time required by the attending physician and the medical center.

Further, conventional approaches to internal imaging and catheter localization require the injection of dye and/or the use of X-rays. Each of these can be harmful to the subject. In addition, such imaging radiation can be harmful to the physicians and staff exposed to the radiation.

The use of such interventional devices is also challenging due to the need to manage several long lengths of wires and other components, including guidewires and catheters, power cables, data wires, and the like. Care must be taken with respect to what is allowed in the sterile field and when it can be removed. Additional staff is often required simply to manage such wires and cables.

As such, there is an ongoing need for improved interventional devices that effectively integrate sensors, effectively manage power and data communication with the sensors, effectively communicate data off of the device for additional processing, and enable more effective positioning of the medical device in the desired target position within the vasculature or other targeted anatomy.

SUMMARY

In one embodiment, a catheter system includes a catheter configured for insertion within a body, the tube structure having a proximal end, a distal end, and a lumen extending therethrough. One or more sensors of one or more sensor types are coupled to the distal section of the tube structure, and one or more wires are associated with the tube structure and are electrically connectable to the one or more sensors. A first power and data coupling device is configured to operably associate with the tube structure and to conductively couple to the one or more wires to thereby send and receive electrical signals through the one or more wires.

In some embodiments, the one or more wires comprise one or more power and/or data lines that extend across or within a wall of the tube structure between the first power and data coupling device and the one or more sensors. The first power and data coupling device can thereby communicate with the one or more sensors at the distal section of the catheter via the one or more power and/or data lines.

In some embodiments, the catheter system includes a first, proximal power and data coupling device disposed at a proximal section of the catheter and a second, distal power and data coupling device disposed at a distal section of the catheter. The catheter is configured to receive a guidewire. The proximal power and data coupling device and the distal power and data coupling device are configured to conductively contact the guidewire when the guidewire is inserted through the lumen of the tube structure to thereby enable passage of the electrical signals between the proximal section of the tube structure and the distal section of the tube structure via the guidewire.

In some embodiments, the proximal power and data coupling device, the distal power and data coupling device, or both are configured to conductively couple to the guidewire through direct contact with the guidewire. In some embodiments, the proximal power and data coupling device, the distal power and data coupling device, or both are configured to conductively couple to the guidewire through capacitive coupling.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 6A-6D illustrate a process for applying a sensor substrate to the distal section of the catheter;

DETAILED DESCRIPTION

Overview of Intraluminal Systems

Figure 1:
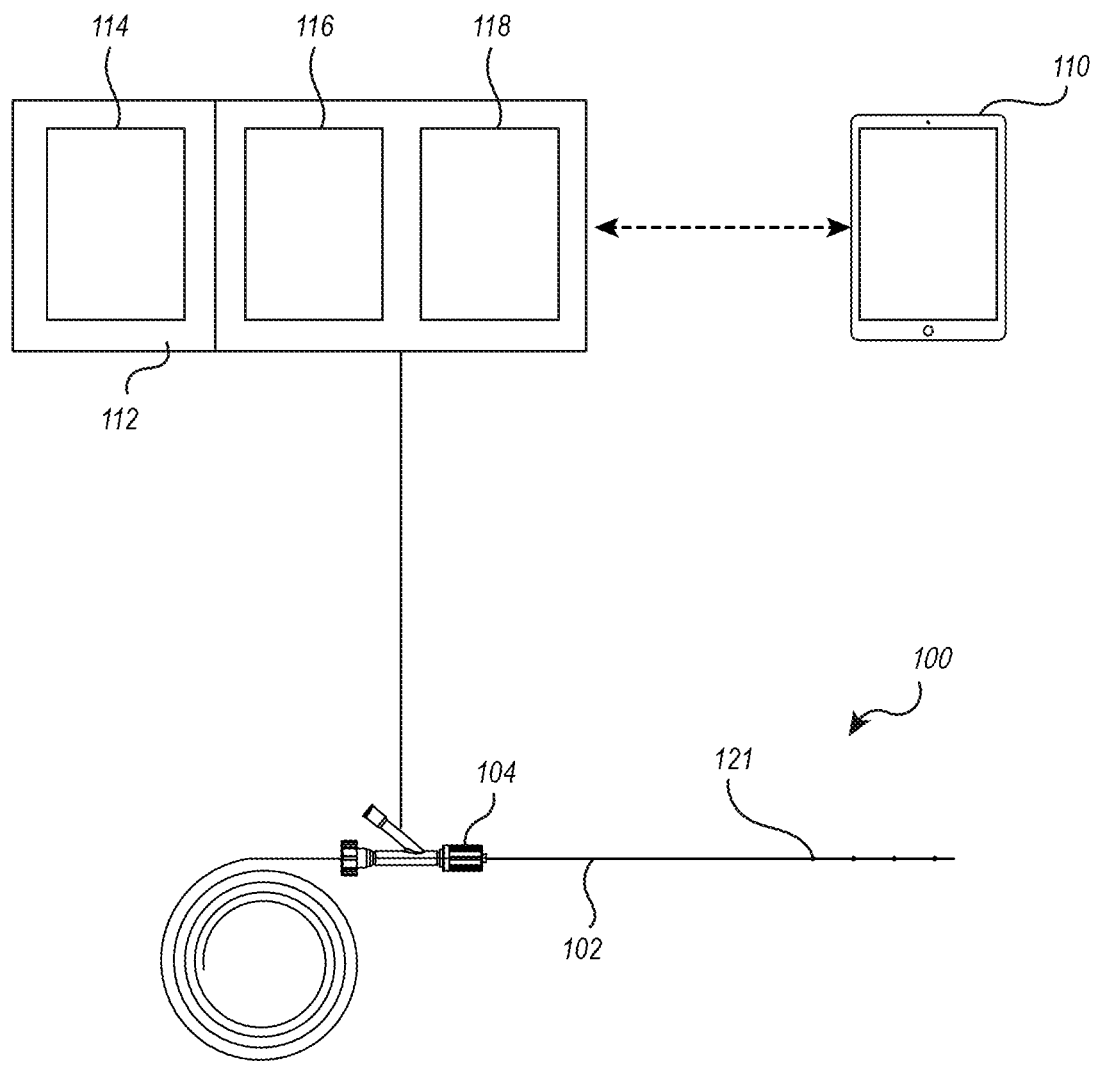
FIG. 1 illustrates a guidewire system configured to provide one or more of the features described herein, showing components of a power and data coupling device and showing that the coupling device may be communicatively coupled to an external device.

FIG. 1 illustrates a schematic overview of a guidewire system 100 that may incorporate one or more of the features described herein. The guidewire system 100 includes a wire 102 that is routable through a proximal device 104. The wire 102 of the guidewire system 100 is configured for insertion into the body of a subject. The subject is typically a human, but in other implementations may be a non-human mammal or even non-mammalian animal. Any suitable route of administration may be utilized, depending on particular preferences and/or application needs. Common routes include femoral, radial, and jugular, but the guidewire system 100 may utilize other access routes as needed.

Although many of the examples described herein relate to use of the guidewire system 100 or the catheter system 200 (see FIG. 2) in relation to intravascular procedures (e.g., cardiovascular or neurovascular), it will be understood that the described systems may be utilized in other medical applications as well. Other medical applications where the systems described herein may be utilized include, for example, applications involving access of the lymphatic, urinary/renal, gastrointestinal, reproductive, hepatic, or respiratory systems.

The proximal device 104 is shown here as a hemostatic valve, though in other embodiments the proximal device 104 may include additional or alternative forms. The proximal device 104 may also be referred to herein as the "data and power coupling device 104" or simply the "coupling device 104".

The length of the wire 102 may vary according to particular application needs and targeted anatomical area. As an example, the wire 102 may have an overall length from proximal end to distal end of about 50 cm to about 350 cm, more commonly about 200 cm, depending on particular application needs and/or particular anatomical targets. The wire 102 may have a size such that the outer diameter (e.g., after application of other outer members) is about 0.008 inches to about 0.040 inches, though larger or smaller sizes may also be utilized depending on particular application needs. For example, particular embodiments may have outer diameter sizes corresponding to standard guidewire sizes such as 0.010 inches, 0.014 inches, 0.016 inches, 0.018 inches, 0.024 inches, 0.035 inches, 0.038 inches, or other such sizes common to guidewire devices. The wire 102 may be formed from stainless steel or other metal or alloy having appropriate mechanical properties. Additionally, or alternatively, the wire 102 may be formed from an electrically conductive material having appropriate mechanical properties. In some embodiments, the wire 102 may be formed of or may comprise a conductive polymer.

The coupling device may also include or be associated with a transmitter to enable wireless communication between the guidewire system 100 and an external device 110 (or multiple such external devices). In alternative embodiments, the guidewire system 100 and external device 110 may be connected via a wired connection.

The external device 110 may be a hand-held device, such as a mobile phone, tablet, or lap-top computer. Although exemplary embodiments are described herein as using hand-held or mobile devices as the external devices 110, it will be understood that this is not necessary, and other embodiments may include other "non-mobile" devices such as a desktop computer, monitor, projector, or the like. In some embodiments, the external device 110 includes a mobile/hand-held device and additionally includes a desktop device or other non-mobile device. For example, a mobile device may be configured to receive transmitted data from the transmitter and function as a bridge by further sending the data to the non-mobile computer system. This may be useful in a situation where the physician would like the option of viewing data on a mobile device, but may need to have the data additionally or alternatively passed or mirrored on a larger monitor such as when both hands are preoccupied (e.g., while handling the guidewire system 100).

The external device 110 of the guidewire system 100 may assist the physician in determining a position of the distal tip of the wire 102 within a vessel or other targeted anatomy of the human body. In this manner, the physician can appropriately position the wire 102 while also obtaining data of various parameters at the targeted anatomy so that the physician can better understand the relevant environment and make appropriate decisions while treating a patient.

The wireless system(s) of the guidewire system 100 and the catheter system 200 may include, for example, a personal area network (PAN) (e.g., ultra-high frequency radio wave communication such as Bluetooth®, ZigBee®, BLE, NFC), a local area network (LAN) (e.g., WiFi), or a wide area network (WAN) (e.g., cellular network such as 3G, LTE, 5G). Wireless data transmission may additionally or alternatively include the use of light signals (infrared, visible radio, with or without the use of fiber optic lines), such as radiofrequency (RF) sensors, infrared signaling, or other means of wireless data transmission.

As used herein, "electrical signals" and "signals" both refer generally to any signal within a disclosed system, device, or method. Whereas, "sensor data signal," "sensor signal," or "data signal" refers to any signal that carries commands or information generated by a medical device, such as a medical sensor. In contrast, "power signal" or "energy signal" refers to any signal that provides power to a medical device, such as a sensor. In some cases, a "signal" may comprise both a data signal and a power signal.

Processing of sensor data signals may be fully or primarily carried out at the external device 110, or alternatively may be at least partially carried out at one or more other external devices communicatively connected to the external device 110, such as at a remote server or distributed network. Additionally, or alternatively, sensor data signals may be processed at the coupling device 104 or 204, on the wire 102 or catheter 202, or at some combination of devices within the guidewire system 100 or catheter system 200. Sensor data signals may include, for example, image data, location data, and/or various types of sensor data (as related to fluid flow, fluid pressure, presence/levels of various gases or biological components, temperature, other physical parameters, and the like).

One or more sensors may be coupled to the wire 102, and the one or more sensors can operate to send data signals through the wire 102 to the coupling device 104. Additionally, or alternatively, the coupling device 104 may operate to send power or signals to the one or more sensors.

As shown, the guidewire system 100 includes a control unit 112 (shown enlarged and in schematic form) that includes a power source 114, data signal processor 116, and optionally a transmitter 118. The transmitter 118 enables wireless communication to the external device 110 (or multiple such devices) as described above.

The data signal processor 116 is configured to receive sensor data signals, sent through the wire 102, from one or more sensors 121 associated with the wire 102. The power source 114 is configured to transmit power through the wire 102 to power the one or more sensors 121 and/or other components of the wire 102. The power source 114 may include an on-board power source, such as a battery or battery pack, and/or may include a wired connection to an outside power source. The one or more sensors 121 may be located at any suitable position on the wire 102, but will typically be disposed at the distal section expected to reach the targeted anatomy.

The guidewire system 100 is configured to send these power and data signals through the actual wire 102 itself, and does not require additional traces/leads for sending signals from distal sections to proximal sections and vice versa. Using the wire 102 itself to send power and/or data signals through the device provides several benefits. For example, using the wire 102 to transmit these signals reduces or eliminates the need to run other connection lines along the wire 102 to connect the sensors 121 to the proximal end and/or to deliver power to the sensors. Given the fact that guidewires inherently involve strict dimensional and performance (e.g., torquability, bending, pushability, stiffness, etc.) limitations and have limited space to work with, the ability to reduce or eliminate extraneous components frees up limited space and allows greater design flexibility. Reducing or eliminating the use of additional connection lines also reduces the overall complexity of the device and thereby reduces the risk of component failure, leading to a more robustly functional device.

Figure 2:
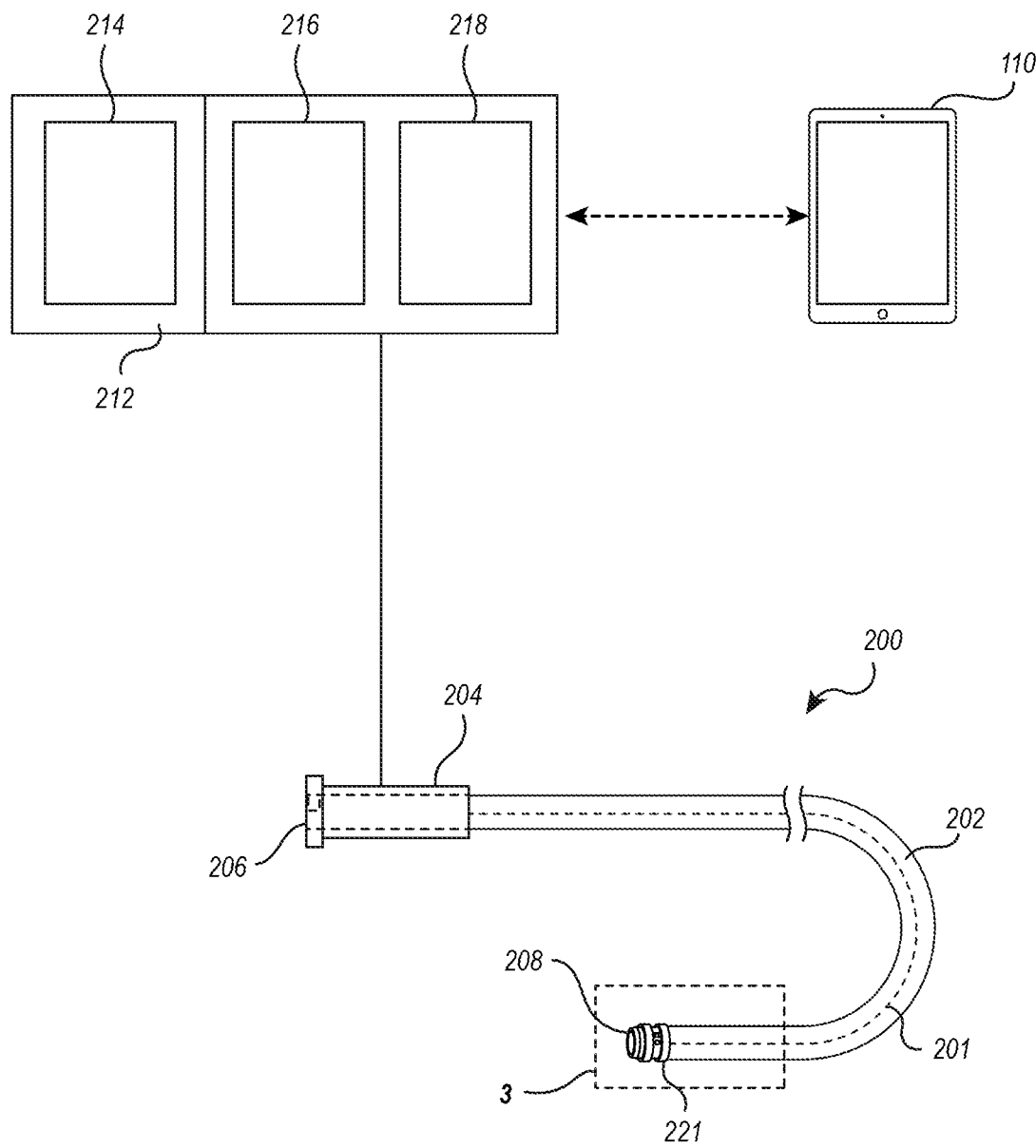
FIG. 2 illustrates a catheter system configured to provide one or more of the features described herein, showing components of a power and data coupling device and showing that the coupling device may be communicatively coupled to an external device.

FIG. 2 is an overview of a catheter system 200 that may incorporate one or more of the features described herein. The catheter system 200 may be similar to the guidewire system 100 in many respects, and the above description related to the guidewire system 100 is also applicable here except where differences are specified. The catheter system includes a catheter 202 that extends from a proximal end 206 to a distal end 208. The catheter 202 may include one lumen or multiple lumens. Typically, the catheter 202 will be formed at least primarily from one or more medical-grade polymer materials, though some embodiments may include other materials such as metals. For example, the term catheter 202, as used herein, can refer to other medical devices that comprise an elongate tube structure, having one or more lumens, configured for insertion into the body, including a hypotube or micromachined tube, unless specified otherwise. In some embodiments the catheter system 200 may include one or more nested catheters (e.g., arranged in a "telescoping" configuration). Separate layers may include, for example, braided layers, liners, polymer coatings, other catheter layers as known in the art, or combinations thereof.

The catheter system 200 includes a catheter 202 and a proximal device 204 (which may also be referred to herein as "the proximal power and data coupling device 204" or just "the proximal coupling device 204"). The proximal coupling device 204 includes a control unit 212 (shown enlarged and in schematic form) that includes a power source 214, data signal processor 216, and optionally a transmitter 218. The transmitter 218 enables wireless communication to the external device 110 (or multiple such devices) as described above with respect to FIG. 1.

The data signal processor 216 is configured to receive sensor data signals, sent through the catheter 202, from one or more sensors 221 associated with the catheter 202. The power source 214 is configured to transmit power through the catheter 202 to power the one or more sensors 221 and/or other components of the catheter 202. The power source 214 may include an on-board power source, such as a battery or battery pack, and/or may include a wired connection to an outside power source. The one or more sensors 221 may be located at any suitable position on the catheter 202, but will typically be disposed at the distal section of the catheter 202 expected to reach the targeted anatomy. As used herein, the "distal section" refers to the distal-most 30 cm of the device, the distal-most 20 cm of the device, the distal-most 15 cm of the device, the distal-most 10 cm of the device, or to a range using any two of the foregoing values as endpoints.

Sensors 221 may be coupled to the catheter 202 (e.g., to the distal section of the catheter 202) by employing bonding, molding, co-extrusion, welding, and/or gluing techniques, for example. Additionally, or alternatively, sensors 221 may be coupled to a substrate which itself is attached to the catheter 202, as explained in more detail below. As used herein, the "distal section" or "distal portion" refers to the distal-most 30 cm of the device, the distal-most 20 cm of the device, the distal-most 15 cm of the device, the distal-most 10 cm of the device, or to a range using any two of the foregoing values as endpoints. In some embodiments, the "intermediate section" may be considered as roughly the middle third of the device, and the "proximal section" or "proximal portion" may be considered as roughly the proximal third of the device.

In some embodiments, power and/or data lines 201 extend along the length of the catheter 202 to the one or more sensors 221. In some embodiments, one or more power and/or data lines 201 may be incorporated into or may form at least a portion of a braid structure within the catheter 202. As used herein, a "power line" and/or "data line" refer to any electrically conductive pathway (e.g., traces) within the medical device. Although multiple power and/or data lines 201 may be utilized, more preferred embodiments are configured to send both power and data on a single wire and/or manage sensor data signals from multiple sensors on a single wire. This reduces the number of wires that must be routed through (or along) the structure of the catheter 202 and more effectively utilizes the limited space of the device, as well as reducing the complexity of the device and the associated risk of device failure.

In some embodiments, multiple power and/or data signals (e.g., data signals from multiple sensors 221) can be sent through a line 201 simultaneously. Power and/or data signals can also be sent in a "continuous" fashion. That is, the power and/or data signals can have a sufficiently high sampling rate such that the information is provided to the user within time frames that are practically "real-time". For most applications, this will include sampling rates of approximately 5 seconds or less, 3 seconds or less, 1 second or less, or sub-second sampling rates.

The proximal coupling device 204 may include one or more ports to facilitate the introduction of fluids (e.g., medications, nutrients) into the catheter 202. The catheter 202 may be sized and configured to be temporarily inserted in the body, permanently implanted in the body, or configured to deliver an implant in the body. In one embodiment, the catheter 202 is a peripherally inserted central catheter (PICC) line, typically placed in the arm or leg of the body to access the vascular system of the body. The catheter 202 may also be a central venous catheter, an IV catheter, coronary catheter, stent delivery catheter, balloon catheter, atherectomy catheter, or IVUS catheter or other imaging catheter. The catheter 202 may be a single or multi-lumen catheter.

The guidewire system 100 and/or catheter system 200 may be effectively utilized in applications where localization of the distal section of the system would be beneficial. For example, localization features described herein may be utilized to aid in stent delivery or proper placement of a PICC catheter or central venous catheter at a targeted site such as the cavoatrial junction.

Additional Sensor Details

The one or more sensors 121 of the guidewire system 100 and/or the one or more sensors 221 of the catheter system 200 may include a pressure sensor, flow sensor, imaging sensor, or a component detection sensor, for example. A pressure sensor (or multiple pressure sensors) may be sized and configured to sense changes in pressure in the environment. A flow sensor (or multiple flow sensors) may be sized and configured to sense the fluid flow, such as velocity or other flow characteristics. A detection sensor (or multiple detection sensors) may detect a proximity or distance to one or more detection nodes positioned external relative to the body. An imaging sensor may gather various forms of imaging data.

The one or more sensors may be additionally or alternatively be configured to sense the presence of biological components or measure physiological parameters in the targeted anatomical location (e.g., in the blood). Example biological components that may be detected/measured include sugar levels, pH levels, $CO_2$ levels ($CO_2$ partial pressure, bicarbonate levels), oxygen levels (oxygen partial pressure, oxygen saturation), temperature, and other such substrates and physiological parameters. The one or more sensors may be configured to sense the presence, absence, or levels of biological components such as, for example, immune system-related molecules (e.g., macrophages, lymphocytes, T cells, natural killer cells, monocytes, other white blood cells, etc.), inflammatory markers (e.g., C-reactive protein, procalcitonin, amyloid A, cytokines, alpha-1-acid glycoprotein, ceruloplasmin, hepcidin, haptoglobin, etc.), platelets, hemoglobin, ammonia, creatinine, bilirubin, homocysteine, albumin, lactate, pyruvate, ketone bodies, ion and/or nutrient levels (e.g., glucose, urea, chloride, sodium, potassium, calcium, iron/ferritin, copper, zinc, magnesium, vitamins, etc.), hormones (e.g., estradiol, follicle-stimulating hormone, aldosterone, progesterone, luteinizing hormone, testosterone, thyroxine, thyrotropin, parathyroid hormone, insulin, glucagon, cortisol, prolactin, etc.), enzymes (e.g., amylase, lactate dehydrogenase, lipase, creatine kinase), lipids (e.g., triglycerides, HDL cholesterol, LDL cholesterol), tumor markers (e.g., alpha fetoprotein, beta human chorionic gonadotrophin, carcinoembryonic antigen, prostate specific antigen, calcitonin), and/or toxins (e.g., lead, ethanol).

Catheter Sensor Arrangement & Distal Features

Figure 3:
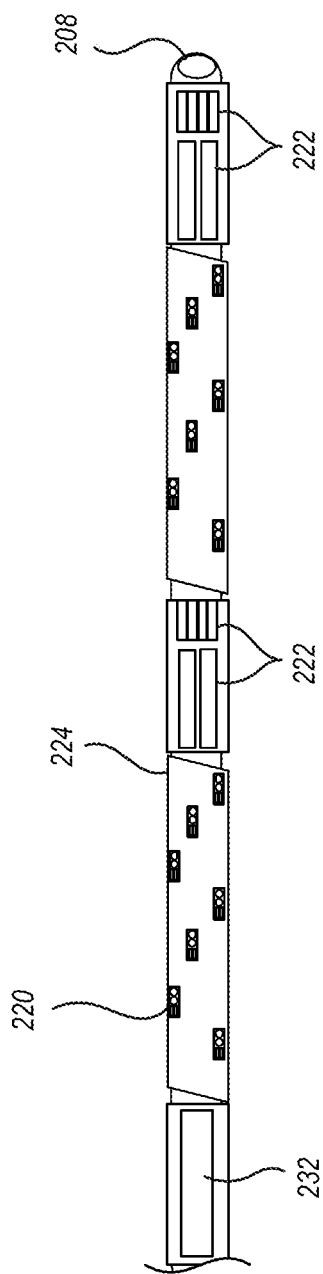
FIG. 3 is an expanded view of a distal section of the catheter to better illustrate exemplary sensor arrangement on the catheter.

FIG. 3 illustrates an expanded view of the distal section of the catheter system 200, showing various sensors arranged thereon. In this embodiment, the one or more sensors 221 (shown more generally in FIG. 2) include multiple pressure sensors 220 and ultrasound sensors 222. As described above, sensors may be attached to the catheter 202 by embedding within the catheter 202, through adhesive attachment, and/or through other means of attachment. In this example, these sensors are positioned on a substrate 224 and the substrate 224 is positioned on the catheter 202 in a manner that places the sensors at their respective desired positions. The substrate 224 can be made of a somewhat flexible material (e.g., a suitable medical grade polymer) that allows wrapping, winding, or otherwise positioning the substrate 224 onto the catheter 202. The substrate 224 also includes flexible circuitry such as trace lines and/or one or more conductive contacts to conductively couple the sensors to the catheter 202. The substrate 224 can form a friction fit with the catheter 202, and can additionally or alternatively be adhered or otherwise mechanically bonded to the catheter 202.

Coupling the sensors to the substrate 224 and then placing the substrate 224 on the catheter 202 provides several benefits. For example, the substrate 224 can be spread into what is essentially a 2-dimensional layout, which makes it much easier to appropriately position the sensors. The 2-dimensional substrate 224, with sensors coupled thereto, can then be placed on the 3-dimensional cylindrical shape of the catheter 202 more readily than placing each sensor separately onto the catheter 202. In particular, it is easier to ensure that the various sensors are appropriately positioned relative to one another on the substrate 224 and then to position the substrate 224 onto the catheter 202 than to attempt to control relative spacing of each sensor on the 3-dimensional cylindrical shape of the catheter 202. Alternatively, the various sensors can be placed on the substrate after the substrate has been applied to the 3-dimensional catheter 202.

The illustrated embodiment also includes an energy harvester 232. The energy harvester is configured to convert injected power into regulated DC voltages suitable for the sensors. The energy harvester 232 can also provide other electrical regulation functions such as cutting power to the sensors during a fault or brownout, for example. Additionally, as used herein and unless specified otherwise, the energy harvester 232 is considered a subcomponent of the one or more sensors 221. As such, unless stated otherwise, references to the one or more sensors 221 also refer to the associated circuitry, such as the energy harvester 232.

Additionally, in at least one embodiment, the energy harvester 232 is configured to provide control functions for the one or more sensors 221. For example, a particular signal can be communicated from the power and data coupling device 204 to the energy harvester 232. The particular signal may comprise a chirp, an impulse function, or some signal at a particular frequency channel. The energy harvester 232 maps the particular signal to a predetermined command and then acts upon that predetermined command. For example, a particular signal may map to a command to cut DC power to one or more rails that are powering one or more sensors 221. As such, upon receiving the particular signal, the energy harvester 232 stops providing power to the one or more sensors 221 causing the one or more sensors 221 to turn off. Any number of different signals may be mapped to any number of different commands. Additionally, in at least one embodiment, a circuit other than the energy harvester 232 receives, interprets, and/or acts upon the signals.

Unless stated otherwise, when reference is made to sensors (either generically or to a specific type of sensor) it should be understood to be inclusive of the supporting electronics as well. Supporting electronics may include, for example, power regulators, converters, signal amplifiers, processing components such as application-specified integrated circuits (ASICs), field-programmable gate arrays (FPGAs), and the like. The supporting electronics of the one or more sensors 221 are preferably positioned near the one or more sensors 221 themselves (e.g., at the distal section and/or on the substrate 224). This was beneficially found to reduce signal drift as compared to placing the supporting electronics at the proximal sections of the device. Placing the supporting electronics (e.g., ASICs) at the distal section near the sensors 221 provides effective signal transmission without the significant drift problems of other approaches.

The length of the catheter 202 that includes the substrate 224 (and thus includes sensors) may be about 3 cm to about 30 cm, or more typically about 5 cm to about 15 cm, though these lengths may be varied according to particular application needs. The length of the sensor arrangement preferably substantially spans the expected length of lesions/stenoses in the target anatomy. The linear arrangement of pressure sensors 220 can be utilized to provide pressure mapping at targeted anatomy without the need to move the catheter 202. Multiple measurements from multiple sensors may be conducted simultaneously and/or continuously. The arrangement of pressure sensors 220 can also be utilized to measure pulse wave velocity (PWV) (e.g., by determining a series of wave peaks and measuring time between peaks) and/or to provide spatial tracking of a pulse waveform.

Catheter Power & Data Transmission Using a Separate Guidewire

Figure 4:
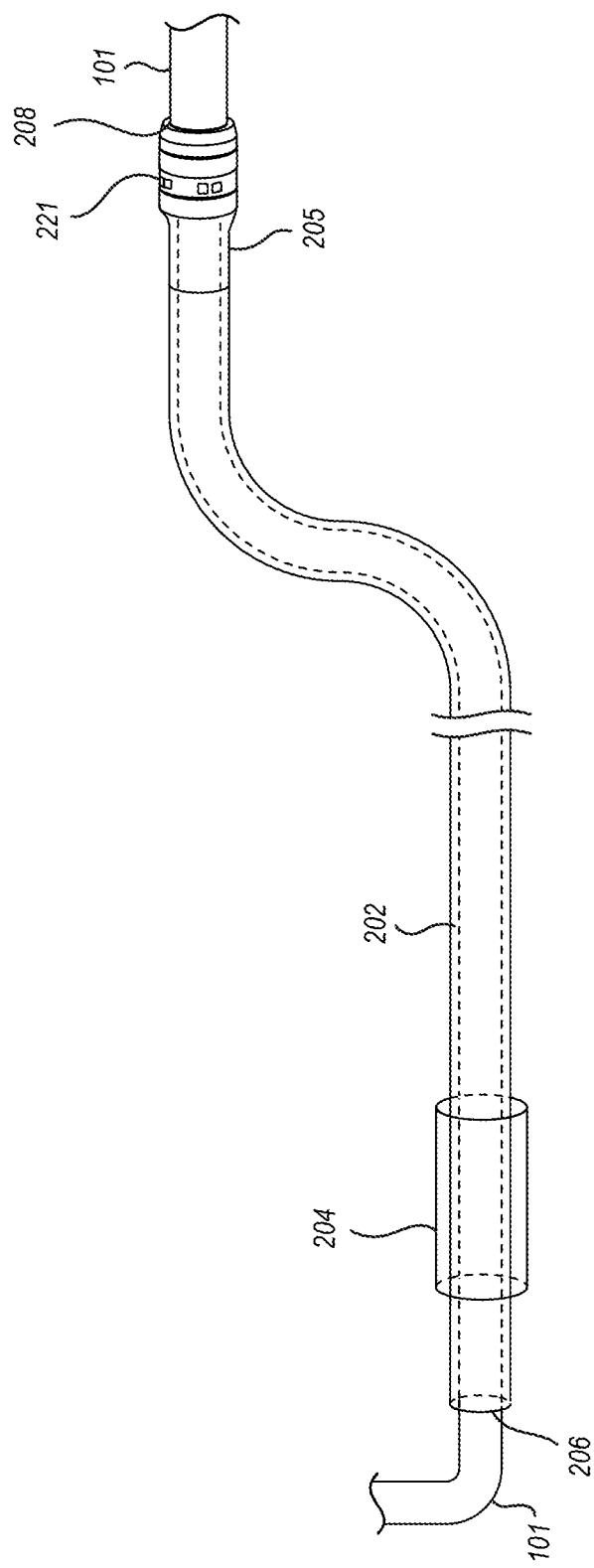
FIG. 4 illustrates the catheter system with components that allow powering of one or more sensors disposed at a distal section and data collection from the one or more sensors using a conductive guidewire passed through the lumen of the catheter.

FIG. 4 illustrates the catheter system 200 in a configuration that allows the one or more sensors 221 to be powered using a conductive guidewire 101 passed through the lumen of the catheter 202 and/or allows the one or more sensors 221 to pass data signals using the guidewire 101. The guidewire 101 may correspond to the guidewire system 100 described above, or may take the form of other guidewires known in the art, so long as the guidewire 101 is capable of conducting electrical signals. Certain embodiments where the catheter 202 is configured to use a guidewire 101 for transmitting power and/or data may omit other power and/or data lines 201. In other words, the catheter 202 may be configured such that the guidewire 101 is the only wire or line necessary for transmitting power and/or data signals.

As shown, the catheter 202 may be routed over the guidewire 101. Both the guidewire 101 and the catheter 202 are routed through the proximal coupling device 204. The one or more sensors 221 are disposed at the distal section of the catheter 202. A distal power and data coupling device 205 (also referred to as "the distal coupling device 205") is also disposed at the distal section of the catheter 202 and is in electrical communication with the one or more sensors 221. Both the proximal coupling device 204 and the distal coupling device 205 are configured to conductively couple to the underlying guidewire 101.

Using the guidewire 101 as the means of transmitting power and/or data reduces or eliminates the need for various power and/or data lines (see power and/or data lines 201 of FIG. 2) in order to transmit power and/or data along the catheter 202. Because such power and/or data lines 201 must be routed alongside the length of the catheter 202 or embedded within the wall of the catheter 202, the shape and mechanical properties of the catheter 202 must account for these additional constraints, and manufacturing is concomitantly made more difficult. Using the guidewire 101 as the means for transmitting power and/or data likewise reduces the number of components at risk of failing or malfunctioning during use of the catheter 202 and thereby provides a robust system for transmitting power to the sensors 221 and receiving data signals from the sensors 221.

The conductive coupling between the coupling devices 204, 205 and the guidewire 101 may be accomplished through direct contact between the coupling devices 204, 205 and the underlying guidewire 101. For example, the inner surfaces of one or both of the coupling devices 204, 205 may be sized so as to directly contact the guidewire 101 as the catheter 202 is passed over the guidewire 101.

More preferred embodiments do not require direct contact with the underlying guidewire 101. As described in more detail below, in some embodiments the proximal coupling device 204, the distal coupling device 205, or both are configured to capacitively couple to the underlying guidewire 101. This type of coupling even further reduces or eliminates the need for various power and/or data lines 201 in order to transmit power and/or data along the catheter 202. Capacitive coupling also eliminates the need to make direct contact between the inner surface of the coupling devices 204, 205 and the outer surface of the guidewire 101, which increases friction and the risk of binding between the catheter 202 and guidewire 101. In other embodiments, the proximal coupling device 204 can be coupled directly to the catheter 202 to transmit power and/or data (without necessarily requiring the guidewire 101 for conductive coupling). Such embodiments do not necessarily need a distal coupling device 205.

Sensor Substrate & Application to Catheter

As described above, the one or more sensors 221 may be coupled to the catheter 202 by embedding within the structure of the catheter 202, by adhesive attachment, and/or through other methods of sensor attachment known in the art. In another example, an outer surface of the catheter 202 may be etched or grooved and filled in with a material (e.g., conductive polymer) that forms appropriate conductive traces to which the one or more sensors 221 may be associated with. An outer layer may then be at least partially applied over the traces and/or sensors 221 to embed the components within the wall of the catheter 202.

The following describes another method of attaching the one or more sensors 221 that may be used in addition to or as an alternative to the other methods of sensor attachment described herein.

Figure 5C:
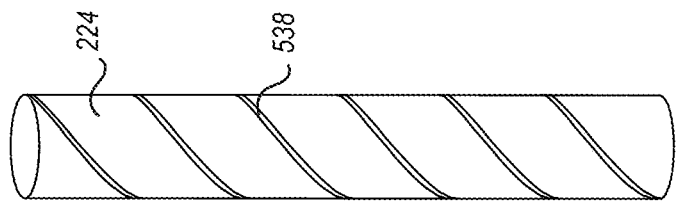
FIGS. 5A-5E illustrate exemplary sensor substrates and various arrangements by which the sensors can be positioned on the catheter using such substrates.
Figure 5B:
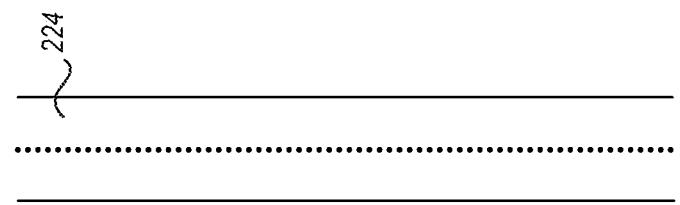
Figure 5A:
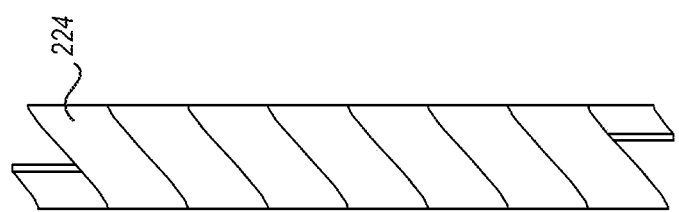

FIGS. 5A-5E illustrate additional exemplary configurations of the substrate 224. FIG. 5A provides an example of the substrate 224 with a structure that allows for spiral wrapping around the catheter 202, similar to what is shown in FIG. 3. FIG. 5B shows an example of the substrate 224 with a cut or split within the structure. The substrate 224 of FIG. 5B may also be positioned around the catheter 202 until edges meet or overlap at the cut/split. Alternatively, the substrate 224 of FIG. 5B may form a "clamshell" structure with two halves that are placed over the catheter 202 and then joined together and/or held in place by an overlying outer member. Although the illustrated cut/split is longitudinal, other embodiments may include other cuts/splits of other shapes, including lateral, curved, helical, and the like. In some embodiments, the cut/split enables a matching interlock and/or set of edges configured to engage with one another when joined.

FIG. 5C shows an example of a substrate 224 with a tube structure and having a cut pattern 538 that allows the tube to be manipulated for placement upon the catheter 202. FIG. 5C shows a spiral cut pattern. Other embodiments may additionally or alternatively include other cut patterns (e.g., a series of longitudinal and/or lateral cuts) that allow the tube to be manipulated to enable placement upon the catheter 202. Preferably, however, the cut pattern 538 is distributed circumferentially about the tube so as to avoid the formation of preferred bending planes within the tube.

Figure 5D:
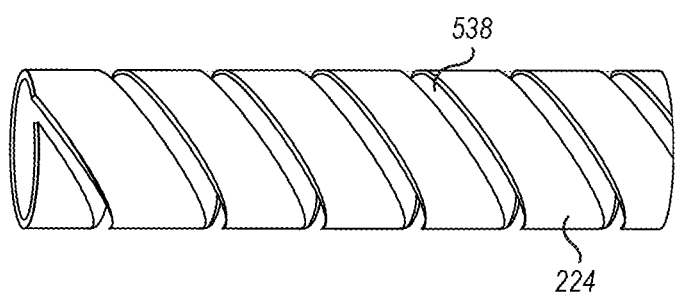
Figure 5E:
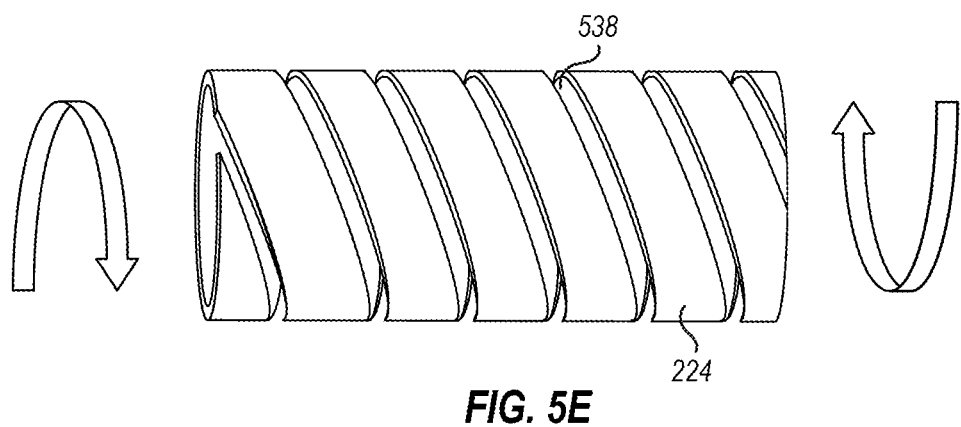

FIGS. 5D and 5E provide an example of how the substrate 224 may be manipulated during placement on the catheter 202. FIG. 5D shows the tube structure of the substrate 224 in its default state. By appropriately twisting the ends of the tube, the tube longitudinally shortens and radially expands, as shown in FIG. 5E. In the radially expanded position, the tube can fit over the catheter 202 and be positioned in the desired location. Upon removal of the twisting force, the tube then reverts to the default position of FIG. 5D, thereby tightening around the catheter 202. In some embodiments, the tube may tighten enough to form a friction fit around the catheter 202. As described above, adhesive bonding and/or placement of an outer member may additionally or alternatively function to hold the substrate 224 in place.

FIGS. 6A-6D illustrate a series of steps for applying the sensor substrate 224 to the catheter 202. In this example, the substrate 224 has the form of a strip configured to be spirally wrapped around the catheter 202 (as in the embodiment shown in FIG. 5A). FIG. 6A shows the substrate 224 laid out in a flat position. The substrate 224 includes a base material 636 (e.g., a suitable medical-grade polymer) and conductive traces 634. The conductive traces 634 may include, for example, standard conductive copper tracing and/or other conductive materials embedded in or otherwise attached to the base material 636.

In some embodiments, a conductive polymer may be utilized to form the conductive traces 634. For example, the base material 636 may be cut, grooved, or otherwise prepared to receive the conductive polymer in the desired locations, and then the conductive polymer may be applied and (as needed) allowed to cure to form the conductive traces 634. A similar process may be applied to an outer surface of the catheter 202 itself, without the need for the substrate 224.

The conductive traces 634 provides a conductive contact for the sensors (e.g., the illustrated pressure sensors 220, though other sensor types described herein may additionally or alternatively be used) so that the sensors 220 can be placed in conductive communication with other components of the underlying catheter 202 once the substrate 224 is applied to the catheter 202. The conductive traces 634 may be formed as one or more continuous and contiguous lines, as shown. Alternatively, one or more discrete sections of conductive material may be included in the substrate 224 for corresponding placement of the sensors, so long as each of the discrete sections are somehow placed in conductive communication with underlying structure.

As shown in FIG. 6B, the sensors 220 are positioned to be rotationally offset from the longitudinal axis of the flattened substrate 224. This allows the sensors to be aligned with the longitudinal axis of the catheter 202 when the substrate 224 is spirally wrapped around the catheter 202, as shown in FIG. 6C. This type of offset may not be necessary for certain sensor types (e.g., sensors that are radially symmetric), but may be utilized where sensor orientation relative to the catheter 202 is important. The offset angle may be about 10 to 35 degrees off of the longitudinal axis, for example, though other offset angles may be utilized depending on factors such as wrapping angle of the substrate 224 when applied to the catheter 202, desired final orientation of the sensors 220, and the like.

The spacing of the sensors 220 upon the substrate 224 and/or the wrapping angle when applying the substrate 224 to the catheter 202 can also be modified to adjust the resulting position and spacing of the sensors 220 relative to the underlying catheter 202. For example, the illustrated embodiment shows that each sequential sensor 220 is circumferentially offset from adjacent sensors by about 120 degrees. Other circumferential offset angles may be utilized according to design preferences and/or particular application needs. Preferred embodiments include some form of circumferential offset in order to better space the sensors 220 about the circumference of the device and therefore better eliminate circumferential position as a variable in the overall sensor readings.

FIG. 6D illustrates application of an outer member 226 over the substrate 224. The outer member 226 may be applied using a shrink tube, through dip coating, and/or through other means of applying polymer coatings to catheters as known in the art. For illustrative purposes, the sensors 220 are shown somewhat above the outer surface of the outer member 226. In most embodiments, the sensors 220 will be substantially flush with the outer surface of the outer member 226.

Imaging Functionality

Figure 7:
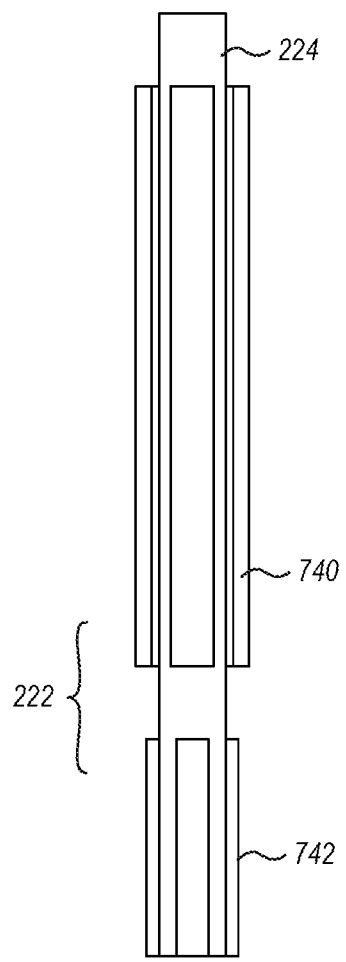
FIG. 7 illustrates a detailed view of an exemplary ultrasound array that may be utilized in the catheter.

The catheter system 200 may include one or more sensors for providing imaging. FIG. 7 illustrates an example of an ultrasound sensor 222. As with other sensors described herein, the ultrasound sensor 222 may be placed on a substrate 224 which is then positioned on the catheter 202, or may be embedded directly into the catheter 202, for example. The illustrated ultrasound sensor 222 includes one or more (preferably multiple) capacitive micromachined ultrasonic transducers (CMUTs) 742 and corresponding supporting electronics in the form of complementary metal oxide semiconductor (CMOS) chips 740. In the illustrated embodiment, each CMUT 742 is associated with its own CMOS chip 740 in a pairwise, 1:1 relationship. Each CMUT 742 and CMOS chip 740 pair works independently to send data signals through the catheter 202, without requiring any of the CMOS chips 740 to multiplex multiple signals from separate CMUTs 742.

Ultrasound sensors 222 of the catheter system 200 may be configured to operate at any appropriate set of frequencies. In some embodiments, the ultrasound sensors 222 are operable with a center frequency of about 10 to about 80 MHz, about 15 to about 60 MHz, about 20 to about 50 MHz, or other ranges using any two of the foregoing values as endpoints.

Some embodiments of the catheter system 200 may additionally or alternatively include other imaging sensors. For example, the catheter system 200 may include camera devices configured to capture various types of imaging data, including pixel arrays, images, video, or other types of imaging data. The catheter system 200 may include any imaging device known in the art suitable for positioning at or integration with a distal portion of the system, including a fiber-optic camera, LIDAR system, Raman scattering system, optical coherence tomography (OCT), mm wave camera, infrared imaging system, other imaging devices/systems known in the art, or combinations thereof. Image data gathered by such an imaging device may be modified using one or more image enhancing algorithms known in the art.

Power & Data Coupling Devices

As described above (see FIG. 4 and related discussion), the catheter system 200 may include a proximal coupling device 204 and distal coupling device 205 that function together to use an underlying guidewire 101 to transmit power and/or data along the catheter 202, thus minimizing or eliminating the need for power and/or data lines 201 extending across significant lengths of the catheter 202. Thus, some embodiments may utilize a single power and data coupling device, and some embodiments may utilize a pair of power and data coupling devices. Some embodiments may include more than two power and data coupling devices. For example, some embodiments may utilize multiple guidewire and/or catheter members (e.g., in a procedure targeting a coronary lesion located at a vessel bifurcation), and a plurality of such members may include one or more power and data coupling devices.

Figure 8A:
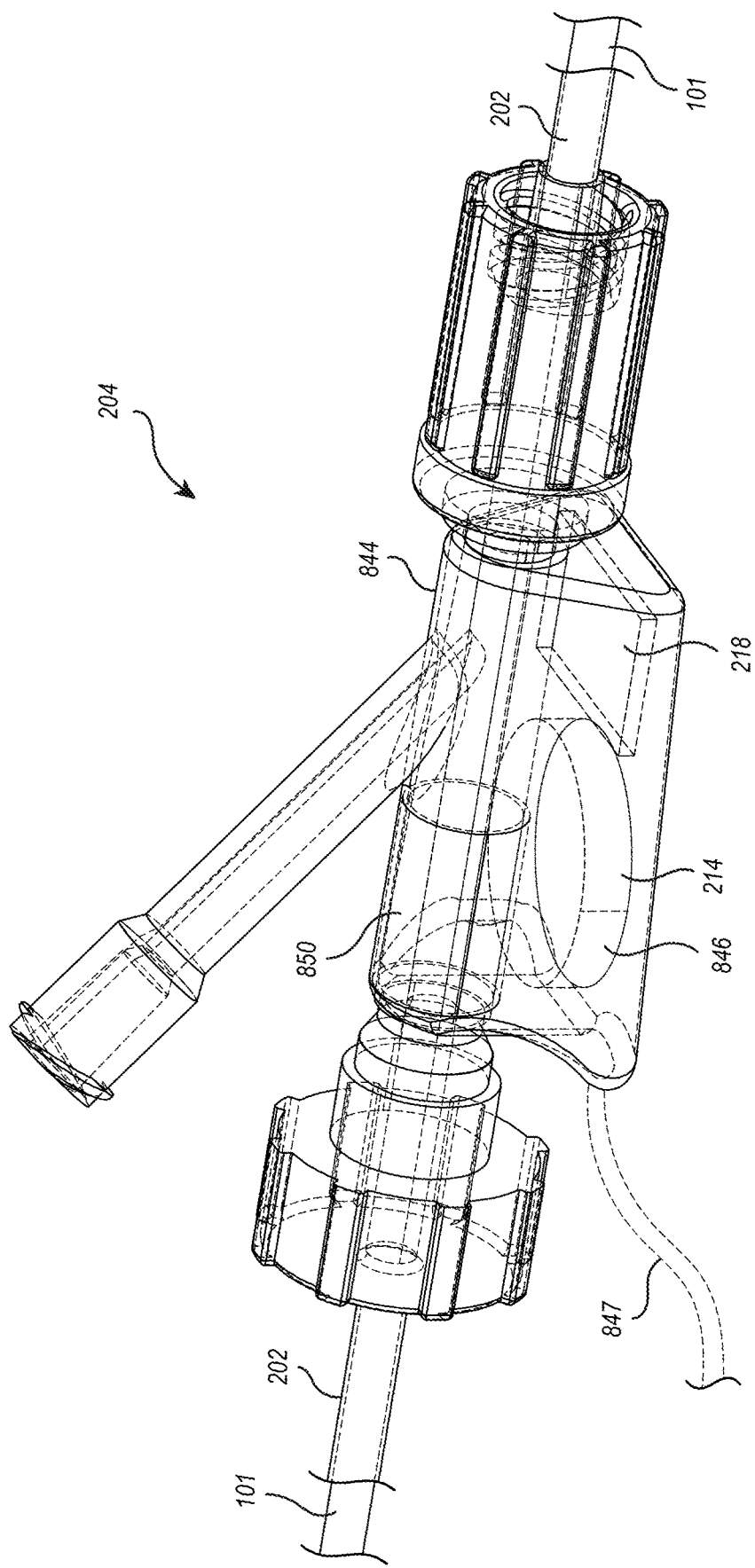
FIGS. 8A and 8B illustrate detailed views of an exemplary proximal power and data coupling device for use at a proximal section of the catheter.

FIG. 8A provides a detailed view of an exemplary proximal power and data coupling device 204. The proximal coupling device 204 is shown here as a hemostatic valve, but the components and associated functions of the proximal coupling device 204 described herein may be provided by other structures (e.g., dilators, ports, insertion needles, syringe) that do not necessarily need to provide valve functionality. However, since hemostatic valves are ubiquitous in guidewire applications, integrating the components of the proximal coupling device 204 into a hemostatic valve is a beneficial implementation.

The illustrated proximal coupling device 204 includes a body 844 that houses the power source (corresponding to power source 214 of FIG. 2) in the form of a battery 846 and the transmitter 218. The proximal coupling device 204 may additionally or alternatively include a wired power connection 847, though preferred embodiments minimize the use of additional wiring. The proximal coupling device 204 also includes a first proximal conductive surface 850 (in the form of a conductive tube in this example) positioned so that the guidewire 101 passes therethrough when inserted and translated through the proximal coupling device 204. FIG. 8A thus illustrates an over-the-wire catheter application in which the catheter 202 can be passed over the guidewire 101 and through the proximal coupling device 204. In such an over-the-wire coupling, the catheter 202 encloses the guidewire 101 at least from the power and data coupling device 204 to the distal portion of the catheter 202. In such embodiments, the catheter 202 is configured to minimize or avoid interference with the capacitive coupling between the proximal coupling device 204 and the guidewire 101. This may be accomplished, for example, by ensuring that the surface of catheter 202 does not completely surround the guidewire 101, including holes or other apertures in the conductive surface (e.g., sized to match the frequencies meant to carry the signal(s) to thereby allow coupling through the gaps).

Figure 8B:
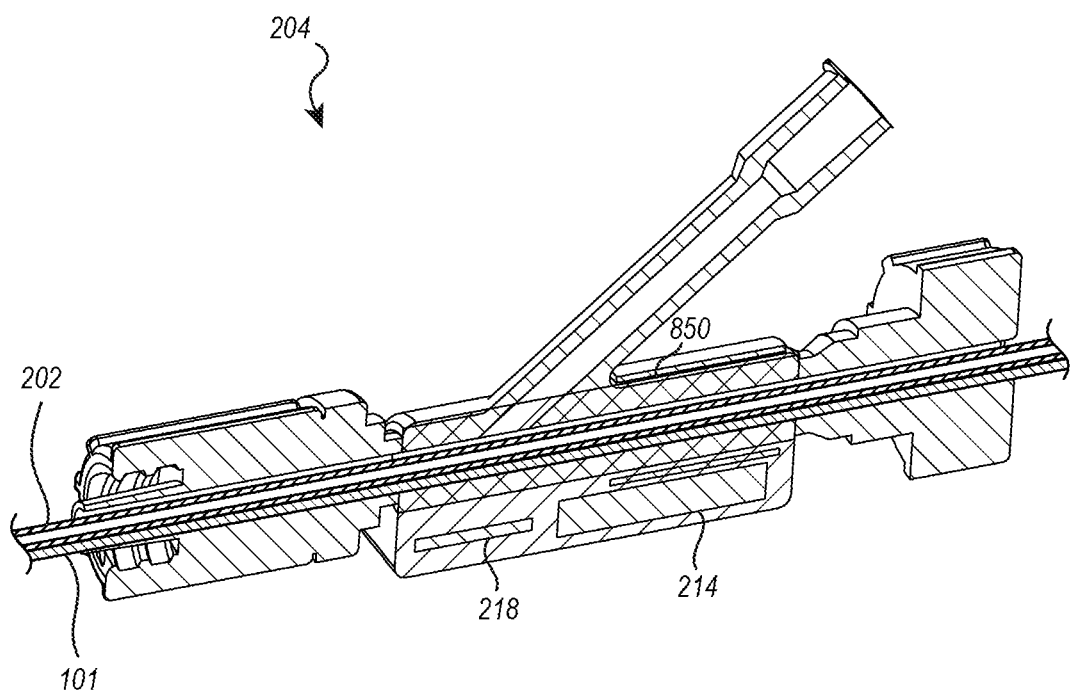

FIG. 8B, on the other hand, depicts the proximal coupling device 204 in a "rapid exchange" catheter application. In this application, the portion of the catheter 202 passing through the proximal coupling device 204 may be adjacent to the guidewire 101 rather than over the guidewire 101. The rapid exchange coupling comprises a distal portion of the catheter 202 enclosing the guidewire 101 and a proximal portion of the guidewire 101 running adjacent to a proximal portion of the catheter 202. In either an over-the-wire or rapid exchange configuration, the power and data coupling device 204 is configured to couple to a conductive surface in the guidewire 101 and/or a conductive surface in the catheter 202.

The illustrated proximal coupling device 204 is configured to function as a capacitive coupler allowing the transfer of power and/or data on and off the catheter 202 (by way of the guidewire 101 in the particular example shown in FIG. 8B; other embodiments do not necessarily require the guidewire 101 to transfer power and/or data and may use, for example, one or more power and/or data lines 201 to transfer power and/or data) without requiring direct contact with the catheter 202 or guidewire 101. In particular, the first proximal conductive surface 850 functions as a first conductive surface configured to couple to a second conductive surface (i.e., a portion of the guidewire 101). In operation, the first proximal conductive surface 850 radiates a time-varying electric field to covey power to the guidewire 101, and includes (or is connected to) a pick-up configured to receive data signals from the guidewire 101 and/or catheter 202. Because the space between the outer surface of the guidewire 101 and the inner portion of the first proximal conductive surface 850 will typically be filled with blood, which has relatively decent conductivity, the capacitive couple can be established without requiring particularly high voltages (e.g., 5 to 12 volts is typically sufficient). The first proximal conductive surface 850 is communicatively connected to the transmitter 218 such that the data signals can be transmitted off the coupling device 204 to one or more external devices 110 (see FIG. 2).

Although the illustrated embodiment includes a first proximal conductive surface 850 in the form of tube, other embodiments may include a first conductive surface in the form of one or more plates, other concentric or partially-concentric shapes, or other shapes capable of forming sufficient electrical contact with the guidewire 101. The proximal coupling device 204 may include one or more additional supporting electronic components such as an amplifier for amplification of signals.

Figure 8C:
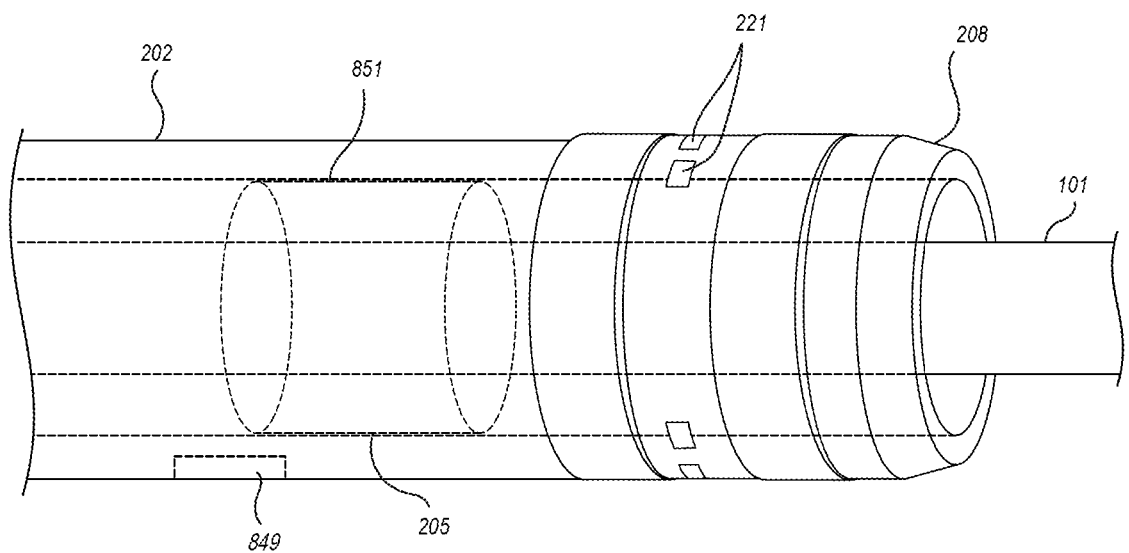
FIG. 8C illustrates a detailed view of an exemplary distal power and data coupling device for use at a distal section of the catheter.

FIG. 8C illustrates an embodiment of the distal coupling device 205 located at the distal section of the catheter 202 (near distal end 208). The distal coupling device 205 may include components and features similar to the proximal coupling device 204 shown in FIG. 8A. The distal coupling device 205 includes a first distal conductive surface 851 (shown here in the form of a tube) through which the guidewire 101 passes, and may optionally include a power source (shown here in the form of battery 849) to which it is electrically connected. The first distal conductive surface 851 may alternatively be a plate, curved surface, or other shape appropriate for use at the distal section of the catheter 202. The one or more sensors 221 are electrically connected to the first distal conductive surface 851 (e.g., by one or more connection lines).

Similar to the proximal coupling device 204, but with signals usually traveling the opposite direction, the first distal conductive surface 851 of the distal coupling device 205 operates to pick up transmitted power signals from the guidewire 101 and then transmits them to the one or more sensors 221. The first distal conductive surface 851 is also configured to receive data signals from the one or more sensors 221 and to radiate a time-varying electric field to covey corresponding data signals to the guidewire 101.

Although the illustrated distal coupling device includes a first conductive surface in the form of first distal conductive surface 851, other embodiments may include a first conductive surface in the form of one or more plates, other concentric or partially-concentric shapes, or other shapes capable of forming sufficient electrical contact with the guidewire 101 at the distal section of the catheter 202. The distal coupling device 205 may include one or more additional supporting electronic components such as an amplifier for amplification of signals.

When the catheter 202 is passed over the guidewire 101 and through the proximal coupling device 204, it does not significantly disrupt the electrical coupling between the first proximal conductive surface 850 and the guidewire 101. Even though the catheter 202 passes between the outer surface of the guidewire 101 and the inner surface of the first proximal conductive surface 850, the capacitive contact is maintained at a level that allows continued transmission of power and data signals (e.g., with appropriate design of the catheter and/or capacitive surface geometry). In contrast, systems that require some type of wired connection to the wire in order to pass power and/or data must be temporarily disconnected when a catheter is routed over a guidewire. In addition to the complications associated with connecting and disconnecting the guidewire, this means that there will be moments where visualization and/or other data signals passed through the wire are stopped. The illustrated system 200, on the other hand, does not require additional disconnection/reconnection steps.

The coupling devices 204, 205 may be configured to simultaneously transmit power and data signals. In some implementations, for example, the proximal coupling device 204 can provide multiple, different power signals to the guidewire 101 (e.g., each power signal configured to power a different sensor or different set of sensors) and/or receive multiple, different data signals from the guidewire 101 (e.g., each data signal from a different sensor or different set of sensors). Similarly, the distal coupling device 205 can provide multiple, different data signals to the guidewire 101 (e.g., each data signal from a different sensor or different set of sensors), and/or receive multiple, different power signals from the guidewire 101 (e.g., each power signal configured to power a different sensor or different set of sensors).

Additional Computer System Details

Certain methods described herein may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web-based services for communicating back and forth with clients.

Many computers are intended to be used by direct user interaction with the computer. As such, computers have input hardware and software user interfaces to facilitate user interaction. For example, a modern general-purpose computer may include a keyboard, mouse, touchpad, camera, etc. for allowing a user to input data into the computer. In addition, various software user interfaces may be available.

Examples of software user interfaces include graphical user interfaces, text command line-based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures, and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Additional Exemplary Aspects

Embodiments of the present disclosure may include, but are not necessarily limited to, features recited in the following clauses:

Clause 1: A medical device, comprising: an elongated tube structure for insertion within a body, the tube structure having a proximal end, a distal end, and a lumen extending therethrough; one or more sensors of one or more sensor types coupled to the distal section of the tube structure; one or more wires associated with the tube structure, the one or more wires being electrically connectable to the one or more sensors; and a first power and data coupling device configured to operably associate with the tube structure, the power and data coupling device configured to conductively couple to the one or more wires and to send and receive electrical signals therethrough.

Clause 2: The medical device of Clause 1, wherein the elongated tube structure is configured as an over-the-wire catheter.

Clause 3: The medical device of Clause 1 or Clause 2, wherein the elongated tube structure is configured as a rapid exchange catheter.

Clause 4: The medical device of any one of Clauses 1-3, wherein the one or more wires comprise one or more power and/or data lines that are disposed within the lumen, or extend across or within a wall of the tube structure between the first power and data coupling device and the one or more sensors.

Clause 5: The medical device of any one of Clauses 1-4, wherein the one or more wires includes a guidewire positionable within at least a portion of the lumen of the tube structure.

Clause 6: The medical device of Clause 5, wherein the first power and data coupling device is a proximal power and data coupling device disposed at a proximal section of the tube structure.

Clause 7: The medical device of Clause 6, further comprising a second, distal power and data coupling device disposed at a distal section of the tube structure.

Clause 8: The medical device of Clause 7, wherein the proximal power and data coupling device and the distal power and data coupling device are configured to conductively contact the guidewire when the guidewire is inserted through the lumen of the tube structure to thereby enable passage of the electrical signals between the proximal section of the tube structure and the distal section of the tube structure via the guidewire.

Clause 9: The medical device of Clause 8, wherein the proximal power and data coupling device, the distal power and data coupling device, or both are configured to conductively couple to the guidewire through direct contact with the guidewire.

Clause 10: The medical device of Clause 8, wherein the proximal power and data coupling device, the distal power and data coupling device, or both are configured to conductively couple to the guidewire through capacitive coupling.

Clause 11: The medical device of Clause 10, wherein the one or more sensors are electrically connected to the distal power and data coupling device at the distal section of the tube structure.

Clause 12: The medical device of any one of Clauses 1-11, wherein the device is configured to send and receive the electrical signals through a single wire.

Clause 13: The medical device of any one of Clauses 1-12, wherein the tube structure is configured as a peripherally inserted central catheter, a central venous catheter, or an intravenous catheter.

Clause 14: The medical device of any one of Clauses 1-13, wherein the first power and data coupling device is configured to conductively couple to the one or more wires through direct contact with the one or more wires.

Clause 15: The medical device of any one of Clauses 1-14 wherein the first power and data coupling device is configured to conductively couple to the one or more wires through capacitive coupling with the one or more wires.

Clause 16: The medical device of any one of Clauses 1-15, wherein the one or more sensor types comprise two or more different sensor types.

Clause 17: The medical device of any one of Clauses 1-16, wherein multiple sensors are configured to provide simultaneous measurement of one or more physiological parameters.

Clause 18: The medical device of any one of Clauses 1-17, wherein the one or more sensors have a sampling rate, when active, of 5 seconds or less.

Clause 19: The medical device of any one of Clauses 1-18, wherein the one or more sensors include one or more pressure sensors.

Clause 20: The medical device of Clause 19, wherein the one or more pressure sensors comprise resistive, capacitive, optical, acoustic, optical-acoustic, or a combination thereof.

Clause 21: The medical device of Clause 19 or Clause 20, the device comprising multiple pressure sensors longitudinally spaced along a length of a distal section of the tube structure.

Clause 22: The medical device of any one of Clauses 1-21, wherein the one or more sensors include one or more ultrasound sensors, cameras, charge-coupled devices, or other imaging detectors.

Clause 23: The medical device of any one of Clauses 1-22, wherein the electrical signals include power signals delivered through the one or more wires to the one or more sensors for powering the one or more sensors.

Clause 24: The medical device of any one of Clauses 1-23, wherein the electrical signals include data signals sent through the one or more wires by the one or more sensors as a result of operation of the one or more sensors.

Clause 25: The medical device of any one of Clauses 1-24, wherein the one or more sensors are embedded at least partially within a wall of the tube structure.

Clause 26: The medical device of any one of Clauses 1-25, wherein the one or more sensors are coupled to a substrate, and wherein the substrate is coupled to a distal section of the tube structure.

Clause 27: The medical device of any one of Clauses 1-26, wherein the one or more sensors and supporting electronics corresponding to the one or more sensors are disposed on a distal section of the tube structure.

Clause 28: The medical device of any one of Clauses 1-27, wherein the tube structure is a hypotube.

Clause 29: A catheter system, comprising: a catheter having a proximal end, a distal end, and a lumen extending therethrough; one or more sensors of one or more sensor types coupled to a distal section of the catheter; a first power and data coupling device configured to operably associate with the catheter; and one or more power and/or data lines that extend across or within a wall of the catheter between the first power and data coupling device and the one or more sensors; wherein the power and data coupling device is configured to capacitively couple to the one or more power and/or data lines and to send and receive electrical signals thereby.

Clause 30: A catheter system, comprising: a catheter having a proximal end, a distal end, and a lumen extending therethrough, the lumen being configured to receive a guidewire; one or more sensors of one or more sensor types coupled to a distal section of the catheter; a proximal power and data coupling device configured to operably associate with a proximal section of the catheter; and a distal power and data coupling device coupled to a distal section of the catheter, wherein the proximal power and data coupling device and the distal power and data coupling device are configured to conductively contact the guidewire when the guidewire is inserted through the lumen of the catheter to thereby enable passage of electrical signals between the proximal section of the catheter and the distal section of the catheter via the guidewire.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A medical device comprising:
   a peripherally inserted central catheter having an elongated tube structure comprising a proximal end, a distal end, and a lumen extending therethrough;
   a set of sensors coupled to a distal section of the tube structure, the set of sensors comprising at least one pressure sensor and at least one imaging sensor;
   a hemostatic valve including a power and data coupling device configured to provide power to, and receive data from, the set of sensors, the power and data coupling device comprising a wireless transmitter; and
   one or more power and/or data lines that extend across or within a wall of the tube structure between the power and data coupling device and the one or more sensors,
   wherein the power and data coupling device is configured to send and receive power and/or data signals through the one or more power and/or data lines, and
   wherein the power and data coupling device is configured to wirelessly communicate with one or more external devices.

2. The medical device of claim 1, wherein the proximal power and data coupling device is configured to transmit data received from the set of sensors to the one or more external devices.

3. The medical device of claim 1, wherein the power and data coupling device is configured to conductively couple to the one or more power and/or data lines through capacitive coupling with the one or more power and/or data lines.

4. The medical device of claim 1, wherein the set of sensors include a plurality of pressure sensors longitudinally spaced along a length of the distal section of the tube structure.

5. The medical device of claim 1, wherein the set of sensors includes one or more ultrasound sensors, cameras, charge-coupled devices, or other imaging sensors.

6. The medical device of claim 1, wherein the proximal power and data coupling device is configured to conductively couple to the one or more power and/or data lines through direct contact with the one or more power and/or data lines.

7. The medical device of claim 1, wherein the power and/or data signals comprise both power signals sent to the set of sensors and data signals sent from the set of sensors.

8. The medical device of claim 7, wherein the catheter is configured to transmit power signals through the one or more power and/or data lines to the set of sensors and data signals through the one or more power and/or data lines to the proximal power and data coupling device simultaneously.

9. The medical device of claim 1, wherein the sensors are embedded at least partially within a wall of the tube structure.

10. A medical device comprising:
    peripherally inserted central catheter having an elongated tube structure comprising a proximal end, a distal end, and a lumen extending therethrough;
    a set of sensors coupled to a distal section of the tube structure, the set of sensors comprising a plurality of pressure sensors longitudinally spaced along a length of the distal section of the tube structure and at least one imaging sensor;
    a hemostatic valve having a power and data coupling device configured to provide power to, and receive data from, the set of sensors, the power and data coupling device comprising a wireless transmitter; and
    one or more power and/or data lines that extend across or within a wall of the tube structure between the power and data coupling device and the set of sensors,
    wherein the power and data coupling device is configured to conductively couple to the one or more power and/or data lines through capacitive coupling with the one or more power and/or data lines and is configured to send and receive power and/or data signals through the one or more power and/or data lines, and
    wherein the proximal power and data coupling device is configured to wirelessly communicate with one or more external devices and to transmit data received from the set of sensors to the one or more external devices.

11. The medical device of claim 10, wherein the set of sensors includes one or more ultrasound sensors, cameras, charge-coupled devices, or other imaging sensors.

12. The medical device of claim 10, wherein the power and/or data signals comprise both power signals sent to the set of sensors and data signals sent from the set of sensors.

13. The medical device of claim 12, wherein the catheter is configured to transmit power signals through the one or more power and/or data lines to the set of sensors and data signals through the one or more power and/or data lines to the power and data coupling device simultaneously.

14. The medical device of claim 10, wherein the sensors are embedded at least partially within a wall of the tube structure.

* * * * *